(12) United States Patent
Stutman (10) Patent No.: US 9,632,040 B2
(45) Date of Patent: Apr. 25, 2017

(54) SYSTEM AND METHOD FOR PHASE-CONTRAST X-RAY IMAGING USING A MULTI-SECTOR SOURCE GRATING

(71) Applicant: The Johns Hopkins University, Baltimore, MD (US)

(72) Inventor: Dan Stutman, Cockeysville, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 40 days.

(21) Appl. No.: 14/701,812

(22) Filed: May 1, 2015

(65) Prior Publication Data

US 2015/0323478 A1 Nov. 12, 2015

Related U.S. Application Data

(60) Provisional application No. 61/990,831, filed on May 9, 2014.

(51) Int. Cl.
| | |
|---|---|
| *G03H 5/00* | (2006.01) |
| *G01N 23/04* | (2006.01) |
| *G01N 23/20* | (2006.01) |
| *A61B 6/00* | (2006.01) |
| *A61B 6/03* | (2006.01) |

(52) U.S. Cl.
CPC ............ *G01N 23/04* (2013.01); *A61B 6/032* (2013.01); *A61B 6/4035* (2013.01); *A61B 6/4291* (2013.01); *A61B 6/484* (2013.01); *A61B 6/5205* (2013.01); *G01N 23/046* (2013.01); *G01N 23/20075* (2013.01); *G01N 2223/33* (2013.01)

(58) Field of Classification Search
CPC .......... A61B 6/00; G03B 42/02; G01N 23/04; G01N 23/00; G01N 23/02
USPC ............................ 378/16, 15, 36, 87, 70, 71
See application file for complete search history.

(56) References Cited

U.S. PATENT DOCUMENTS

| | | | |
|---|---|---|---|
| 2011/0243300 A1 | 10/2011 | Kaneko et al. | |
| 2013/0028378 A1* | 1/2013 | Stutman | G01N 23/04 378/62 |
| 2013/0034209 A1* | 2/2013 | Ouchi | A61B 6/484 378/62 |
| 2013/0202081 A1* | 8/2013 | Rossl | A61B 6/484 378/36 |
| 2014/0037054 A1 | 2/2014 | Yamaguchi et al. | |
| 2014/0112400 A1 | 4/2014 | Reuven | |
| 2014/0226785 A1* | 8/2014 | Stutman | G01N 23/046 378/36 |

FOREIGN PATENT DOCUMENTS

WO 2013-111050 A1 8/2013

OTHER PUBLICATIONS

International Search Report dated Aug. 17, 2015 from International Application No. PCT/U52015/028758, pp. 1-10.

(Continued)

*Primary Examiner* — Wyatt Stoffa
*Assistant Examiner* — Jason McCormack
(74) *Attorney, Agent, or Firm* — MH2 Technology Law Group LLP (57) ABSTRACT

A differential phase contrast X-ray imaging system includes an X-ray illumination system, a beam splitter arranged in a radiation path of the X-ray illumination system, and a detection system arranged in a radiation path to detect X-rays after passing through the beam splitter.

18 Claims, 5 Drawing Sheets

(56) References Cited

OTHER PUBLICATIONS

Stutman D., Finkenthal M., "Glancing angle Talbot-Lau grating interferometers for phase contrast imaging at high x-ray energy", Applied Physics Letters, 2012 (101), pp. 091108-1-091108-5.
A. Sarapata, J. W. Stayman, M. Finkenthal, J. H. Siewerdsen, F. Pfeiffer and D. Stutman "High energy x-ray phase contrast CT using glancing-angle grating interferometers", Medical Physics, Feb. 2014, 41(2), pp. 021904-1-021904-9.
Stutman, D. et al. High Energy X-ray Phase-Contrast Imaging Using Glancing Angle Grating Interferometers. Proc. SPIE 8668, Medical Imaging 2013: Physics of Medical Imaging, Mar. 19, 2013, pp. 866814-1-866814-8.
Zanette, I. et al. Interlaced phase stepping in phase-contrast x-ray tomography. Applied Physics Letters, 2011 (98), pp. 094101-1-094101-3.
Stutman, Dan et al. K-edge and mirror filtered X-ray grating inteferometers. International Workshop on X-Ray and Neutron Phase Imaging With Gratings, Tokyo, Japan, 2012 AIP Conf. Proc. 1466, pp. 229-236.
Bravin, Alberto et al. X-ray phase-contrast imaging: from pre-clinical applications towards clinics. Physics in Medicine and Biology, 2013 (58), pp. R1-R35.

\* cited by examiner

SYSTEM AND METHOD FOR PHASE-CONTRAST X-RAY IMAGING USING A MULTI-SECTOR SOURCE GRATING

CROSS REFERENCE TO RELATED APPLICATIONS

This application claims priority to and the benefit of the U.S. Provisional Patent Application having Ser. No. 61/990,831, filed on May 9, 2014, titled "System and Method for Phase-Contrast X-Ray Imaging," to Dan Stutman, the entirety of which is incorporated by reference herein. This application is also related to U.S. patent application Ser. No. 13/493,392, titled "Differential Phase Contrast X-ray Imaging System and Components," filed on Jan. 31, 2013, U.S. patent application Ser. No. 14/174,830, titled "Systems and Method for Phase-Contrast X-Ray Imaging," filed on Feb. 6, 2014, U.S. patent application Ser. No. 14/176,655 titled "Large Field of View Grating Interferometers for X-ray Phase Contrast Imaging and CT at High Energy," filed on Feb. 10, 2014 by Dan Stutman and Michael Finkenthal, hereby incorporated by reference in their entirety.

FIELD

This disclosure relates to X-ray systems, and more particularly to differential phase contrast X-ray imaging systems and X-ray illumination systems.

BACKGROUND

X-ray differential phase-contrast (DPC) imaging relies on the refraction of the X-rays passing through an object. Since for hard X-rays the refraction angles are in the μ-radian range, the basic technique used for DPC imaging is to angularly filter with μ-radian resolution the transmitted X-ray beam, thus converting the angular beam deviations from refraction into intensity changes on a conventional detector. The angular filtering is done using X-ray optics such as crystals or gratings.

A fundamental advantage of DPC imaging is that it is sensitive to density gradients in the measured object rather than to its bulk X-ray absorption. In medical imaging for instance, refraction has a contrast enhancing effect at soft tissue boundaries, which enables the detection of soft tissues which are otherwise invisible in conventional X-ray imaging. The ultra-small angle scattering occurring in micro-structured soft tissue such as cartilage, tendon, ligament or muscle has also a volume contrast enhancing effect. Another benefit of DPC for medical imaging is that it can improve contrast and resolution at similar or lower dose than in conventional X-ray imaging. This is possible because DPC uses X-rays that are not absorbed by the body and because the soft tissue refraction coefficients decrease with X-ray energy much slower than the absorption ones. In particular, by using for DPC a spectrum with mean energy in the 50-80 keV range approximately, the soft tissue dose is minimized while refraction strongly dominates over absorption.

X-ray phase-contrast is also of interest for imaging and non-destructive characterization in material sciences, in particular as concerns low-Z materials. The structure and defects of materials ranging from polymers, to fiber composites, to wood, and to engineered bio-materials can be probed on the micrometer scale using X-ray phase-contrast. Some of the techniques used for X-ray phase-contrast can also be applied with neutrons. Recently X-ray phase-contrast has gained attention in fusion energy research, where the capability of refraction based imaging to measure the density gradients in an object can be used for the diagnostic of high density plasmas in inertial confinement fusion (ICF) and other high energy density physics (HEDP) experiments.

Until recently, research on X-ray DPC imaging has been done mostly at synchrotrons, using crystal optics; the high intensity of the synchrotron compensates for the low efficiency (less than a hundredth of a %) of the crystal optics. Although there are efforts to develop table-top synchrotrons, or to use narrow $K_\alpha$ lines from conventional tubes, the crystal method has not yet entered the domain of practical applications. It is thus of interest to develop more efficient DPC methods and optics, that can work with conventional medical or industrial X-ray tubes.

A DPC method that can work with conventional X-ray sources is the Talbot-Lau shearing interferometry, in which micro-periodic optics such as gratings are used to angularly filter the refracted X-rays with μ-radian resolution. The Talbot interferometer includes first a 'beam-splitter' (typically a π-shift phase grating), which divides (or 'shears') through the Talbot effect the incoming beam into few μ-radian wide beamlets. The Talbot effect consists in a 'replication' of the grating pattern by the wave intensity, at periodic distances along the beam, called Talbot distances, $d_T = k/\eta^2 \cdot g^2/(2\lambda)$, with λ the X-ray wavelength, g the grating period, k=1,2, ... the order of the pattern, and η=1 for a π/2 phase shifting grating or for an absorption grating, and η=2 for a π phase grating. The beamsplitter thus creates at the 'Talbot distance' a micro-periodic fringe pattern, which changes shape (shifts) with respect to the unperturbed pattern when a refractive object is introduced in the beam. The differential phase-contrast imaging consists thus in measuring the changes in the fringe pattern induced by the object, with respect to the pattern without the object. To achieve μ-radian angular sensitivity at hard X-ray wavelengths, the period g must be in the μm range, resulting in a Talbot distance of a few tens of cm.

The fringe pattern can in principle be directly measured using a microscopic pixel detector. This is however quite inefficient. For most practical applications, the fringe pattern changes are converted into intensity changes on a macroscopic pixel detector by introducing an 'analyzer' absorption grating placed behind the beam-splitter and having the period of the Talbot pattern. Lastly, for such an interferometer to function with an extended spot X-ray tube, a 'source' absorption grating is placed in front of the source, thus dividing it into an array of quasi-coherent line sources.

The gratings are made by micro-lithography in thin Si wafers or photoresist. The absorption gratings are difficult to fabricate; they are typically made by filling with gold the gaps in regular transmission gratings. The 'grating shearing method' described above has demonstrated performance similar to the crystal method at energies below a few tens of keV.

Figures 1A, 1B:
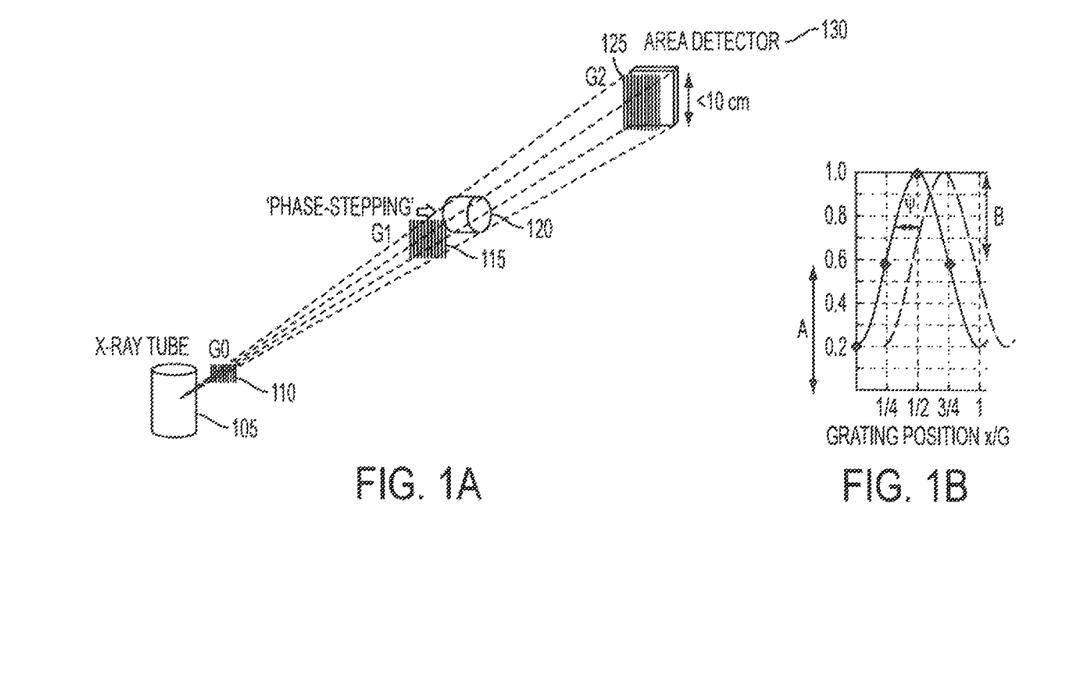
FIGS. 1A and 1B illustrate a layout of conventional grating based phase contrast radiography and the inset illustrates the phase-stepping curve for N=4 steps, obtained by scanning one of the gratings along its period, respectively. Only small objects can be imaged and multiple successive exposures are required to obtain the phase-stepping curve.

This method is however less useful at energies above a few tens of keV. The reason is that it is difficult to fabricate micron-period absorption gratings with the thickness required to block higher energy X-rays. This is illustrated in FIG. 1A with a plot of the Au thickness needed for 95% absorption, as a function of the photon energy. As seen, several hundred μm depth gratings would be needed in the range of interest for clinical DPC imaging. Depending on the grating period, the present technological limit is however around 50-100 μm. This limits the contrast of the grating shearing method for high energy X-rays, as illustrated in FIG. 1B by the fringe contrast computed for an interferometer having 100 μm thick, 4 μm period Au analyzer grating (throughout this specification we used for X-ray phase-contrast and optics calculations the XWFP wave propagation code and the XOP optics package).

SUMMARY

In accordance with the present teachings, a method for phase contrast imaging of an object using an interferometer comprising a multi-sector source grating, a beam-splitter grating, and an analyzer grating, wherein the object is positioned between the beam-splitter grating and the analyzer grating is provided. The method can comprise directing an X-ray beam onto the multi-sector source grating, wherein each sector of the multi-sector source grating is offset by a predetermined amount; obtaining multiple images during a single expose by translating the object or the interferometer, wherein the multiple images have a different interferometer phasing; and combining the multiple images that were obtained to produce a phase contrast image of the object.

In accordance with the present teachings, a device for phase contrast imaging of an object is provided. The device can comprise an interferometer comprising a multi-sector source grating, a beam-splitter grating, and an analyzer grating, wherein the object is positioned between the beam-splitter grating and the analyzer grating; an X-ray source operable to direct an X-ray bean onto the multi-sector source grating, wherein each sector of the multi-sector source grating is offset by a predetermined amount; a translation mechanism operable to translate the object or the interferometer; a detector operable to obtaining multiple images of the object during a single expose; and a processor operable to combine the multiple images that were obtained to produce a phase contrast image of the object.

In some aspects, the multi-sector source grating has greater than three different sectors.

In some aspects, the multiple images are acquired at different angles through the object.

In some aspects, the interferometer has a length about 1.8 m.

In some aspects, the analyzer grating has a thickness of about several tens of centimeters.

In some aspects, the multiple images are obtained using a line or slot scan detectors separated by about 1 cm that is positioned behind the analyzer grating.

In some aspects, an angle between the multiple images is about 0.3°.

In some aspects, an angular range between four images is about 0.9°.

In some aspects, the analyzer grating comprises multiple glancing angle grating stacked in order to cover a length of a detector.

INCORPORATION BY REFERENCE

The following references are incorporated by reference in their entirety.
[1] Alberto Bravin, Paola Coan and Pekka Suortti
[2] "X-ray phase-contrast imaging: from pre-clinical applications towards clinics" Phys. Med. Biol. 58 (2013) R1-R35
[3] Stutman D., Finkenthal M., "Glancing angle Talbot-Lau grating interferometers for phase contrast imaging at high x-ray energy", Appl. Phys. Lett. 101, 091108 (2012)
[4] D. Stutman; J. W. Stayman; M. Finkenthal; J. H. Siewerdsen "High energy x-ray phase-contrast imaging using glancing angle grating interferometers" Proc. SPIE 8668, Medical Imaging 2013: Physics of Medical Imaging, 866814 (Mar. 19, 2013)
[5] A. Sarapata, J. W. Stayman, M. Finkenthal, J. H. Siewerdsen, F. Pfeiffer and D. Stutman "High energy x-ray phase contrast CT using glancing-angle grating interferometers" In print in Medical Physics 2014
[6] Zanette, M. Bech, F. Pfeiffer, and T. Weitkamp, "Interlaced phase stepping in phase-contrast x-ray tomography" Appl. Phys. Lett. 98, 094101 (2011)
[6] www.teledynedalsa.com/imaging/products/x-ray/scanning/argus/
[7] www.dectris.com/
[8] D. Stutman and M. Finkenthal "K-edge and mirror filtered X-ray grating interferometers" INTERNATIONAL WORKSHOP ON X-RAY AND NEUTRON PHASE IMAGING WITH GRATINGS, Tokyo, Japan, 2012 AIP Conf. Proc. 1466, pp. 229-236

BRIEF DESCRIPTION OF THE DRAWINGS

The accompanying drawings, which are incorporated in and constitute a part of this specification, illustrate embodiments of the disclosure and together with the description, serve to explain the principles of the disclosure. In the figures.

DETAILED DESCRIPTION OF THE EMBODIMENTS

Reference will now be made in detail to exemplary embodiments of the disclosure, examples of which are illustrated in the accompanying drawings. Wherever convenient, the same reference numbers will be used throughout the drawings to refer to the same or like parts.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less that 10" can assume negative values, e.g. −1, −2, −3, −10, −20, −30, etc.

Embodiments of the present disclosure relate to the use of multiple grating Interferometers (GAIs) viewing each a separate slice through an object, to make X-ray phase contrast scanning radiography (PC-SR) systems over a broad energy range, from <20 keV, to >100 keV.

Embodiments of the present disclosure are a further advancement of our previous disclosure, the Glancing Angle grating Interferometer (GAI, patent application PCT/US12/41908), and discloses a simple and economical method for X-ray phase-contrast radiography of large objects such the human torso.

Applications envisaged for embodiments of the present disclosure are in medical X-ray imaging, where PC was shown to strongly enhance the visibility of soft tissues, such cartilage, tendon, blood vessels, arterial plaque, brain tissue, micro calcifications, and tumors. The systems described in accordance with embodiments of the present disclosure can work with high energy X-rays and with high power and extended spot medical X-ray tubes, thus enabling X-ray phase-contrast radiography of tissues deep in the human body.

In addition, embodiments of the present disclosure can be used in the field of industrial non-destructive testing (NDT) and security screening, where the disclosed systems can be implemented also by scanning the object instead of the interferometers.

The imaging modalities for soft tissues are MRI, ultrasound, and X-rays. However, while MRI and ultrasound provide good soft tissue contrast, their spatial resolution is limited. Conventional (attenuation based) X-ray imaging on the other hand has good spatial resolution, but poor soft tissue contrast.

X-ray differential phase-contrast (PC) or refraction based imaging with grating interferometers has the potential to become a new medical imaging modality, offering higher soft tissue contrast and spatial resolution than that obtained with conventional attenuation based imaging. For instance, recent analysis suggests that PC-CT could enable the detection of small tumors and lesions in soft tissue, which is not possible with other imaging modalities. X-ray phase contrast diagnostic of arterial plaque or of cartilage damage appears also possible. There is thus a rapidly growing spectrum of possible medical applications of X-ray PC [1]. In addition, there could be many powerful applications of X-ray phase-contrast in non-destructive testing and material sciences.

FIGS. 1A and 1B illustrate a layout of conventional grating based phase contrast radiography. The inset illustrates the phase-stepping curve for N=4 steps, obtained by scanning one of the gratings along its period. Only small objects can be imaged and multiple successive exposures are required to obtain the phase-stepping curve.

The Glancing Angle Interferometer (GAI) consists of three micro-period gratings: 'source', 'beam-splitter', and 'analyzer', having equal period and separated by equal distances, and inclined at an angle typically in the range 10-30°. The role of inclining the gratings is to increase their effective thickness from the normal incidence value t, to $t/\sin(\alpha)$ and thus achieve high interferometer fringe contrast or visibility over a broad energy range, exceeding 100 keV[2]. Multiple GAIs can be stacked and tiled to make large field of view (FOV) imaging systems [3].

Our previous disclosures focused on X-ray phase contrast Computed Tomography (PC-CT). While CT is a powerful technique for 3-D imaging, most of the medical, as well as industrial and security imaging is still done in radiographic mode, i.e. using plain 2-D projections. The advantages of radiography are simplicity, speed, low cost, and high spatial resolution at clinically compatible X-ray dose. For instance, breast radiography or mammography is the 'gold standard' modality for breast cancer screening.

It is thus of value to develop phase contrast radiography in addition to CT. There are however several problems to be solved:

i) The area that needs to be covered in radiography (e.g. 25×25 cm in mammography, and up to 40 cm×60 cm in chest or abdomen radiography) is larger than the grating area possible with present technology (<100 cm$^2$). Combining tens of such gratings to cover an area of a few thousand cm$^2$ is difficult in practice and would also be costly.

ii) Phase contrast imaging requires acquiring multiple images (a minimum three) of an object to produce the attenuation, refraction, and scatter radiographs. Acquiring these images in temporal succession (i.e. through multiple exposures) as it is usually done, is impractical for medical or industrial radiography because of potential patient/object movement. In addition, acquiring successive images implies having the whole object in the interferometer field of view, i.e. covering a large area with gratings, which as above mentioned is difficult and costly.

iii) The conventional grating interferometer has poor fringe contrast at the high X-ray energies needed to image thick body parts such as the torso, head or legs (>70-80 kVp).

iv) The extent of the FOV in the direction perpendicular to the grating bars only a few cm for all grating interferometers, including the GAI, because of the collimating (vignetting) effect of the narrow and deep grating openings [3]. Cylindrically curved gratings can be made to alleviate the vignetting effect, but they are expensive and also do not solve the problem of imaging at high X-ray energy.

v) At low X-ray energies (mammography range), where conventional normal incidence interferometers can work, it would still be advantageous to use the GAI design, in order to improve the grating uniformity and reduce manufacturing costs. For instance, research grade gratings can be made with period of ~2.5 μm and with thickness of ~50 μm, adequate for work up to ~35 kVp. However, such high aspect-ratio gratings are difficult to make and have poor quality. It is much easier and of better quality to make the gratings with ~25 μm thickness and use them in a GAI setup at 30° angle, thus doubling their effective thickness.

In some implementations, the combination of three or more GAI interferometers is disclosed so as to make low cost, scanning phase contrast radiography (PC-SR) systems for all energies of practical interest, that do not require successive exposures, and that can image large objects with high resolution and with clinically compatible dose and scanning speed.

Accordingly, embodiments consistent with the present teachings disclose the following features. The use of multiple (≥3) closely spaced spatial views or chords through an object, having each a different interferometer phasing, to obtain the phase-contrast radiographs, instead of multiple temporally separated images (i.e. sequential exposures). The use of a line or slot scanning design to nearly simultaneously acquire the multiple images needed for phase contrast imaging, thus alleviating the patient/object motion problem. The use of multiple spatial views together with a line or slot scanning design to acquire phase contrast radiographs of large objects (up to several tens of cm wide, by meters long). The use of 'multi-phased' gratings, having multiple sectors or active areas with lines shifted with a fraction of the grating period from sector to sector, to obtain the multiple images needed for phase contrast radiography, without the need to scan one of the gratings or for successive exposures. The use of multi-view scanning GAI interferometers for phase contrast radiography of large objects, up to high (150 kVp) X-ray energy. The use of multi-view scanning GAI interferometers in conjunction with TDI (Time Delay Integration) detectors or with photon counting detectors, for phase contrast mammography and radiography with low dose and high speed. The use of mirror or reflector filtered multi-view scanning GAI interferometers, for quasi-monochromatic phase contrast radiography with very high sensitivity and low dose.

FIG. 1A shows a layout of conventional grating-based phase contrast radiography. FIG. 1b shows a phase-stepping curve for N=4 steps that is obtained by scanning one of the gratings of FIG. 1A (source grating G0 or beam-splitter grating G1) along its period. In the arrangement of FIG. 1A, only small objects can be imaged and multiple successive exposures are required to obtain the phase-stepping curve of FIG. 1B. Conventional grating phase contrast imaging works by placing the entire object in a Talbot-Lau normal incidence interferometer and then laterally scanning one of the gratings across its period, with N steps of size x=G/N, where G is the grating period. Successive images are acquired for each grating position.

As shown in FIG. 1A, the conventional grating-based phase contrast radiography system 100 operable to image an object 120 comprises an x-ray source 105, i.e., x-ray tube, a source grating G0 110, a beam-splitter grating G1 115, an analyzer grating G2 125, and an area detector 130. The source grating G0 110 is positioned between the x-ray source 105 and the beam-splitter grating G1 115. The object 120 is positioned between the beam-splitter grating G1 115 and the analyzer grating G2 125. Typically, the area detector 130 is less than 10 cm on a side. This arrangement process produces a quasi-sinusoidal intensity oscillation in each pixel of the image, named 'phase-stepping' curve, as shown in FIG. 1B:

$$I(n)=A+B\cdot\sin(n\cdot x/G\cdot 2\pi+\phi)\ n=1,2,\ldots N$$

The dc or mean value A of the phase-stepping curve produces the attenuation image, the amplitude of the modulation B the scatter image, and the phase shift φ introduced by the object to the refraction image [1].

Since the phase-stepping curve is determined by three parameters, a minimum number of three phase steps, with three corresponding interferometer images are needed to obtain the attenuation, refraction and scatter images of the object.

This method requires having the entire object in the interferometer field of view. For large objects, such as the human torso, this is difficult, because the typical grating size is 5 several by several cm. In addition, the grating field of view in the direction perpendicular to the grating bars (horizontal in FIG. 1A), is limited to a few cm by the collimating effect of the narrow and deep grating openings. The method also requires acquiring multiple successive images, which requires a long measurement time (typically several tens of seconds with a medical tube), and also requires that the object does not move during this time. These constraints limit the practical usefulness of the conventional phase contrast imaging method, in particular for medical radiography. In addition, the conventional normal incidence interferometer works only at low X-ray energy (<40 kVp typically).

Figures 2A, 2B:
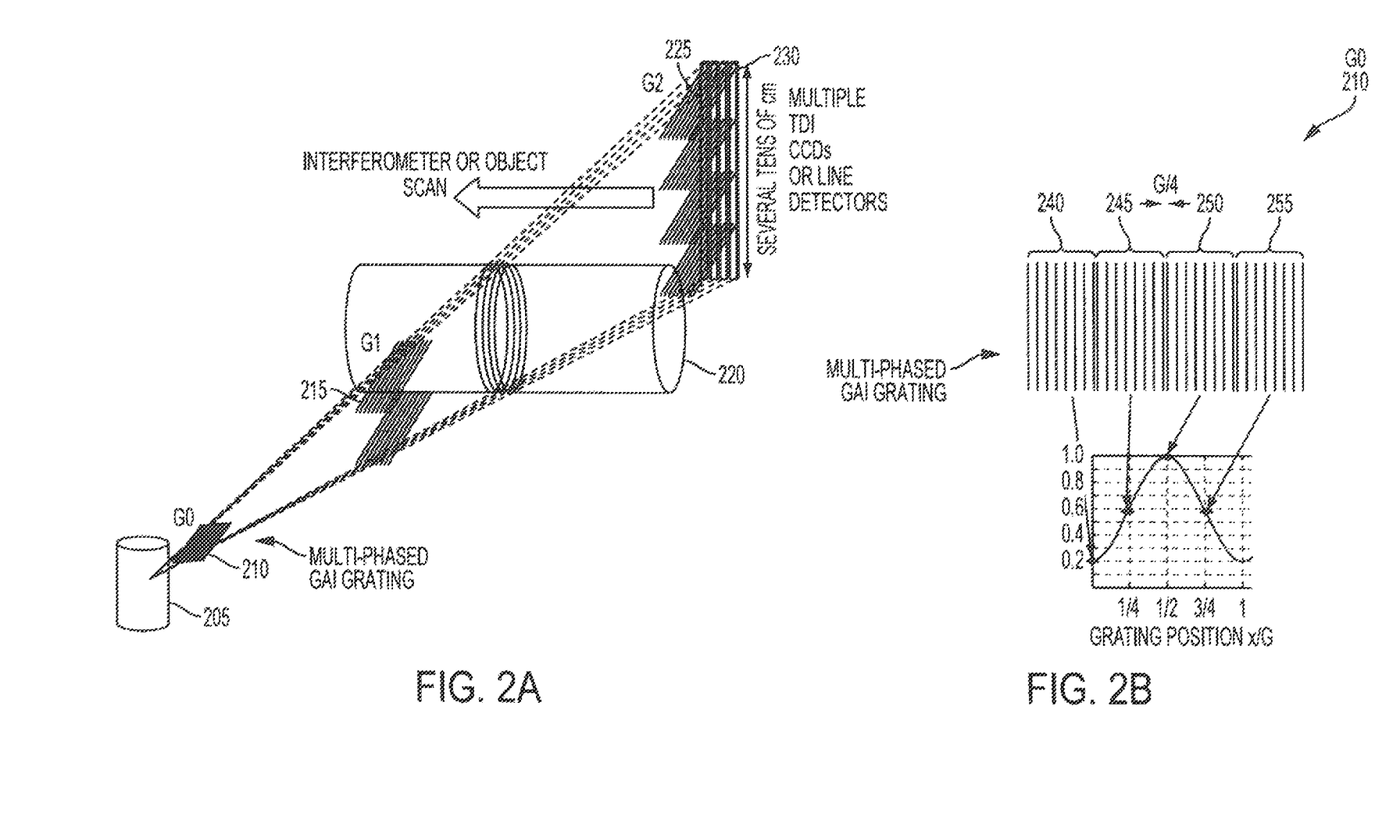
FIGS. 2A and 2B illustrate an example layout, based on embodiments. Stacked glancing angle interferometer ("GAI") gratings can be used to image a long and narrow field of view, while the object or the interferometer is scanned. Multiple (≥3), closely spaced views through varying phase interferometers can be used to obtain the equivalent of the phase-stepping curve, without the need for multiple exposures. The varying interferometer phasing can be achieved using a multi-sector or 'multi-phased' grating, in this sketch the source grating, G0.

FIG. 2A illustrates an example grating-based phase contrast radiography system, based on embodiments. Stacked GAI gratings are used to image a long and narrow field of view, while the object or the interferometer is scanned. Multiple (≥3), closely spaced views through varying phase interferometers are used to obtain the equivalent of the phase-stepping curve, without the need for multiple exposures. The varying interferometer phasing is achieved using a multi-sector or 'multi-phased' grating, which in FIG. 2A, is the source grating, G0. The multi-sector source grating, G0, can have at least two different sectors.

As shown in FIG. 2A, the example grating-based phase contrast radiography system 200, according to embodiments, which is operable to image an object 220 comprises an x-ray source 205, i.e., x-ray tube, a source grating G0 210, a beam-splitter grating G1 215, an analyzer grating G2 225, and a detector 230. The source grating G0 210 is positioned between the x-ray source 205 and the beam-splitter grating G1 215. The object 220 is positioned between the beam-splitter grating G1 215 and the analyzer grating G2 225. In some aspects, the analyzer grating G2 225 can have a thickness of about several tens of centimeters. The analyzer grating can comprises multiple glancing angle grating stacked in order to cover a length of the detector 230. The detector 230 can comprise multiple Time Delay Integration (TDI) CCD detectors or line detectors.

The example arrangement as shown in FIGS. 2A and 2B can solve, in a cost effective manner, all of the above problems. In the example arrangement, multiple, closely spaced fan views or 'slices' through the object are used in order to acquire the multiple images needed for phase contrast imaging. Each view has a different phasing of the interferometer, obtained using a grating with multiple regions or sectors 240, 245, 250, and 255, each having different relative line position, as shown in FIG. 2B. For instance, if four views are used, the relative phasing of the grating lines between sectors would be 0, G/4, G/2, and 3G/4, where G is the grating period. Any of the three gratings can be split in sectors, but the easiest to manufacture in this way is the small size source grating, G0.

By scanning the fan views or slices across the object (by translating either the object or the interferometer), multiple images having each a different interferometer phasing are acquired almost simultaneously (the only time lag being the distance between the adjacent views divided by the scan speed, which for a typical radiographic setup is a fraction of a second). The multiple images are acquired at different angles through the object and these images are then used to build the phase-stepping curve, as shown in FIG. 2B.

In this example approach, the phase contrast radiography images acquired at slightly different angles through the object are used. For instance, assuming a typical interferometer length of ~1.8 m and line or slot scan detectors separated by 1 cm, the angle between views is 0.3°. Assuming four views, one phase contrast projection would thus average the phase information over a 0.9° angular range.

Ours and other studies of 'interlaced' phase contrast rotational tomography [4], in which images acquired at slightly different CT angles are used for phase retrieval similar to FIG. 2 [5,6], show however that such a small angular averaging is not significantly affecting the accuracy or quality of the refraction images. The attenuation and scatter images are even less affected by this small angular averaging.

In addition, embodiments of the present disclosure can use long and narrow slot or line scanning detectors, with multiple GAI gratings stacked in order to cover the length of the detector. This will enable radiography of large objects through linear scanning with a wide fan beam. For instance, Teledyne Dalsa produces for panoramic X-ray imaging 7 mm wide, by up to 440 mm long TDI CCDs [6]. (TDI or Time Delay Integration is a technique for obtaining line scan images with very high signal-to-noise ratio and consists in shifting the charge accumulated in the CCD synchronous with the object scan. The TDI CCD works in essence as a continuous film cassette.) Using such detectors, one could easily scan an object of the size of the human leg or torso. Alternately, one could use closely spaced rows of linear detectors such as photon counting Si or CdTe pixilated arrays [7]. This would also add energy resolution to the system, enabling to further increase its sensitivity and performance.

Figure 3A:
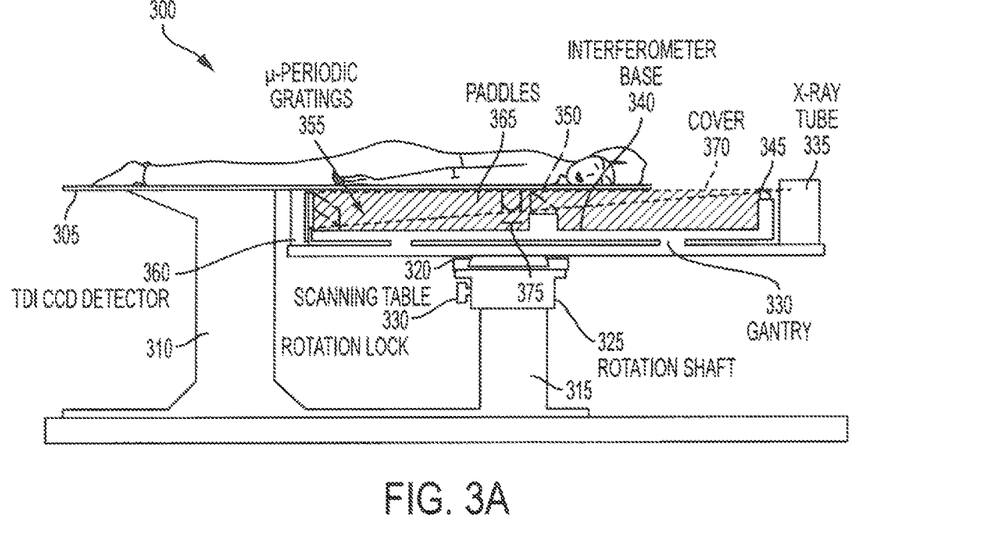
FIG. 3A illustrates an example side view of scanning phase contrast mammography system, according to embodiments and 3B illustrates a top view. The attenuation, refraction, and scatter images are simultaneously obtained in a single pass of the linear scanning table. To enable the cranio-caudal (CC), medio-lateral oblique (MLO), and medio-lateral projections required in mammography the interferometer gantry can rotate on the support shaft.
Figure 3B:
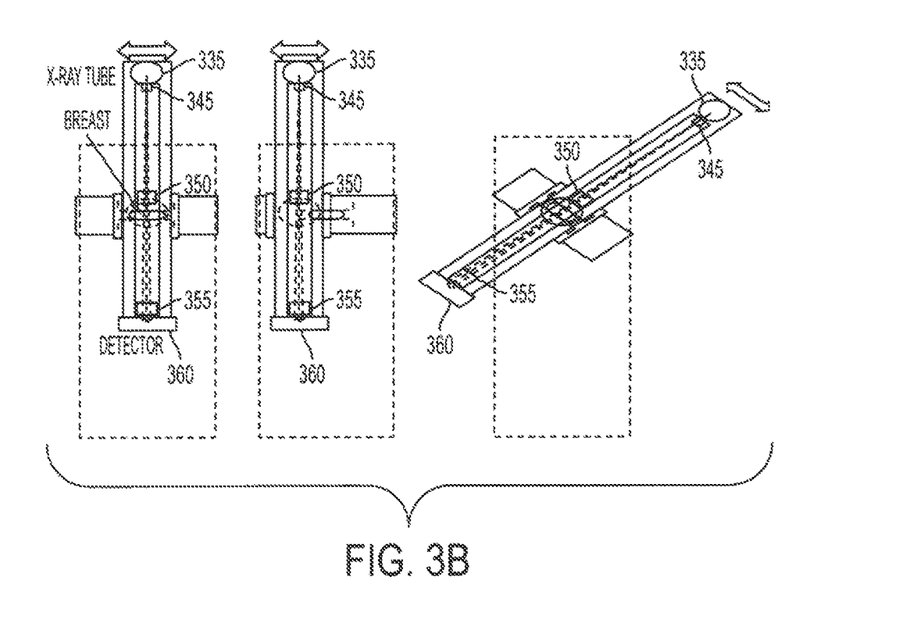

FIG. 3A illustrates an example side view of scanning phase contrast mammography system, according to embodiments and 3B illustrates a top view. The attenuation, refraction, and scatter images are simultaneously obtained in a single pass of the linear scanning table. To enable the cranio-caudal (CC), medio-lateral oblique (MLO), and medio-lateral projections required in mammography the interferometer gantry can rotate on the support shaft.

In this embodiment, a low energy PC-SR mammography system 300 is disclosed that operates at low X-ray energy. In the example layout is shown in FIGS. 3a and 3b, the low energy PC-SR mammography system 300 comprises a patient supporting member 305 that is supported by a first base member 310 and a second base member 315. A scanning table 320 is positioned below the patient supporting member 305 and above the second base member 315. The scanning table 320 is operable to rotate using a rotation shaft 325 coupled to the second base member 315 and is abled to be locked into a position using a rotation lock 330 coupled to the rotation shaft 325. The scanning table 320 is arranged below the patient supporting member 305 and comprises a gantry 330. The gantry 330 comprises an x-ray source 335, i.e., x-ray tube, and a GAI, similar to that described above in relation to FIGS. 2a and 2b, that is supported by an interferometric base 340. As discussed in relation to FIGS. 2a and 2b, the interferometric base 340 supports source gratings (G0) 345, beam-splitter gratings (G1) 350, analyzer (G2) gratings 355, and a detector 360, i.e., TDI CCD detector. In this arrangement, the breast tissue, which is the object being scanned, can be supported on either side by a pair of paddles 365. The top of the gantry 330 can be covered with a cover 370.

With the patient lying prone on the patient supporting member 305 with an opening 375 for the breast, this position is similar to the position used in stereotactic biopsy imaging systems. The prone position allows also having the breast immersed in an index of refraction matching fluid (e.g. saline or water), so as to remove the strong phase variation occurring for low X-ray energies at the breast/air interface. Due to the collimated geometry the estimated dose with such a system is low, of the order of 1 mGy, and the scan time is only several seconds. As described in a previous disclosure [8], an X-ray mirror or other band-pass spectral filter can be added to the system to produce a quasi-monochromatic spectrum which will further enhance the performance of the interferometers and lower the dose.

Figure 4A:
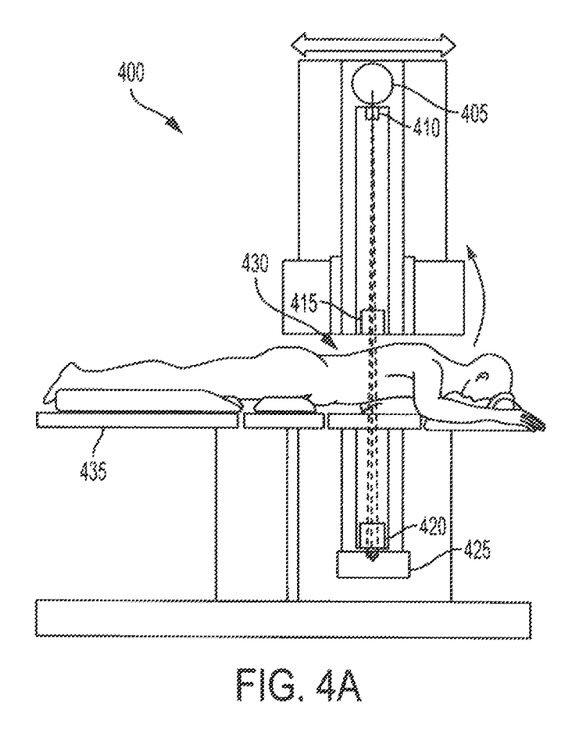
FIGS. 4A and 4B illustrate an example scanning phase contrast radiography system for the whole-body in front view and side view, respectively, according to embodiments. For added tomosynthesis capability, the scanning table can also rotate around the patient.
Figure 4B:
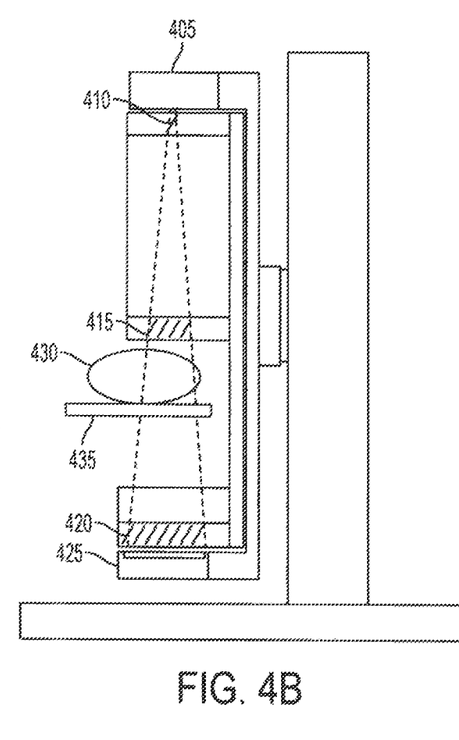

FIGS. 4A and 4B illustrate an example front and side view scanning phase contrast radiography system 400 for the whole-body, respectively, according to embodiments. The system 400 comprises a GAI, similar to that described above in relation to FIGS. 2a and 2b, and similar to that described above in relation to FIGS. 3A and 3B except that the GAI in FIGS. 3A and 3B are in a horizontal arrangement, the GAI of FIGS. 4A and 4B is in a vertical arrangement. The GAI comprises an x-ray source 405, source gratings (G0) 410, beam-splitter gratings (G1) 415, analyzer gratings (G2) 420, and a detector 425, i.e., TDI CCD detector. The patient being scanned is positioned on a table 435 and the portion of the body being scanned 430 is positioned between the beam-splitter gratings (G1) 415 and the analyzer gratings (G2) 420. For added tomosynthesis capability the scanning table can also rotate around the patient. In this example, a high energy PC-SR system is disclosed for whole-body radiography (chest, abdomen, extremities or head). This embodiment uses a similar layout as for PC-SR mammography, but with thicker and more inclined gratings that can work at up to 140 kVp energy, and with longer (up to several tens of cm) scanning detectors. Such PC-SR systems will enable soft tissue X-ray diagnostic throughout the body at high energy, similar to the way mammography enables detecting soft tissues abnormalities in the breast at low energy. An example high impact application could be for instance X-ray phase contrast diagnostic of unstable arterial plaque. Recent research shows that X-ray phase contrast can discriminate very well between the arterial wall, low density lipid deposits, and fibrous or calcified plaque capsule.

Embodiments of the present disclosure are possible also for industrial or security phase contrast imaging, where wide and long objects, such as luggage or helicopter blades, can be scanned in the field of view of the interferometer.

In operation, the systems depicted in FIGS. 3A and 3B and FIGS. 4A and 4B using the system depicted in FIGS. 2A and 2B can be operable to perform a method for phase contrast imaging of an object using an interferometer comprising a multi-sector source grating, a beam-splitter grating, and an analyzer grating, wherein the object is positioned between the beam-splitter grating and the analyzer grating. The method can comprise directing an X-ray beam onto the multi-sector source grating, wherein each sector of the multi-sector source grating is offset by a predetermined amount; obtaining multiple images during a single expose by translating the object or the interferometer, wherein the multiple images have a different interferometer phasing; and combining the multiple images that were obtained to produce a phase contrast image of the object. The multiple images can be obtained using a line or slot scan detectors separated by about 1 cm that is positioned behind the analyzer grating. The angle between the multiple images can be about 0.1°, about 0.3°, or about 0.5°. The angular range between four images can be about 0.5°, about 0.7°, 0.9°, or about 0.11°. Other angles between the multiple images and other angular ranges between image can be used depending on the particular configuration of the imaging system used.

The foregoing description is illustrative, and variations in configuration and implementation can occur to persons skilled in the art. For instance, the various illustrative logics, logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but, in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

In one or more exemplary embodiments, the functions described can be implemented in hardware, software, firmware, or any combination thereof. For a software implementation, the techniques described herein can be implemented with modules (e.g., procedures, functions, subprograms, programs, routines, subroutines, modules, software packages, classes, and so on) that perform the functions described herein. A module can be coupled to another module or a hardware circuit by passing and/or receiving information, data, arguments, parameters, or memory contents. Information, arguments, parameters, data, or the like can be passed, forwarded, or transmitted using any suitable means including memory sharing, message passing, token passing, network transmission, and the like. The software codes can be stored in memory units and executed by processors. The memory unit can be implemented within the processor or external to the processor, in which case it can be communicatively coupled to the processor via various means as is known in the art.

Figure 5:
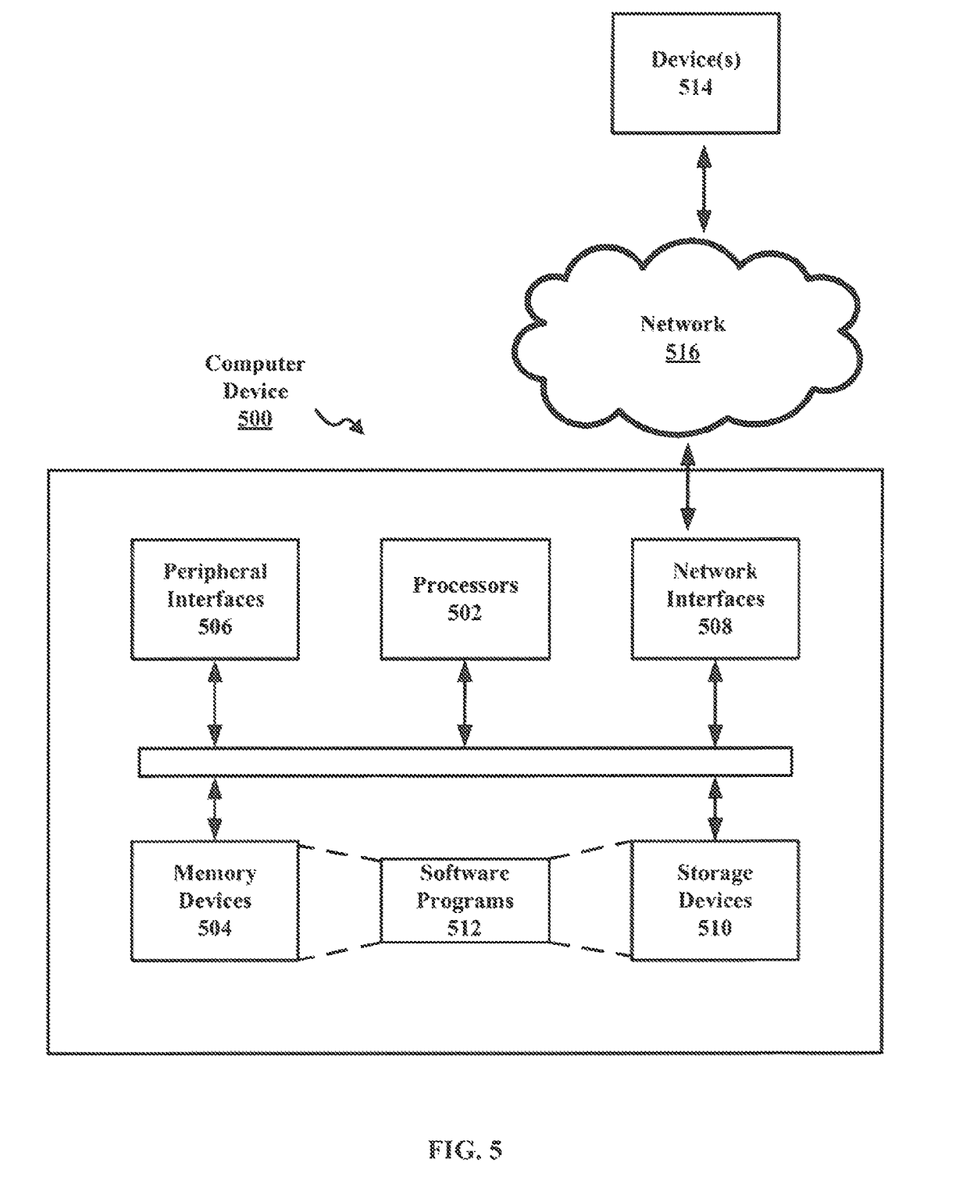
FIG. 5 illustrates an example computer system, according to embodiments.

For example, FIG. 5 illustrates an example of a hardware configuration for a computer device 500, that can be used to perform one or more of the processes of the features described above. While FIG. 5 illustrates various components contained in the computer device 500, FIG. 5 illustrates one example of a computer device and additional components can be added and existing components can be removed.

The computer device 500 can be any type of computer devices, such as desktops, laptops, servers, etc., or mobile devices, such as smart telephones, tablet computers, cellular telephones, personal digital assistants, etc. As illustrated in FIG. 5, the computer device 500 can include one or more processors 502 of varying core configurations and clock frequencies. The computer device 500 can also include one or more memory devices 504 that serve as a main memory during the operation of the computer device 500. For example, during operation, a copy of the software that supports the features can be stored in the one or more memory devices 504. The computer device 500 can also include one or more peripheral interfaces 506, such as keyboards, mice, touchpads, computer screens, touchscreens, etc., for enabling human interaction with and manipulation of the computer device 500.

The computer device 500 can also include one or more network interfaces 508 for communicating via one or more networks, such as Ethernet adapters, wireless transceivers, or serial network components, for communicating over wired or wireless media using protocols. The computer device 500 can also include one or more storage device 510 of varying physical dimensions and storage capacities, such as flash drives, hard drives, random access memory, etc., for storing data, such as images, files, and program instructions for execution by the one or more processors 502.

Additionally, the computer device 500 can include one or more software programs 512 that enable the functionality of the features described above. The one or more software programs 512 can include instructions that cause the one or more processors 502 to perform the processes described herein. Copies of the one or more software programs 512 can be stored in the one or more memory devices 504 and/or on in the one or more storage devices 510. Likewise, the data utilized by one or more software programs 512 can be stored in the one or more memory devices 504 and/or on in the one or more storage devices 510.

In implementations, the computer device 500 can communicate with one or more other devices 514 via a network 516. The one or more other devices 514 can be any types of devices as described above. The network 516 can be any type of network, such as a local area network, a wide-area network, a virtual private network, the Internet, an intranet, an extranet, a public switched telephone network, an infrared network, a wireless network, and any combination thereof. The network 516 can support communications using any of a variety of commercially-available protocols, such as TCP/IP, UDP, OSI, FTP, UPnP, NFS, CIFS, AppleTalk, and the like. The network 516 can be, for example, a local area network, a wide-area network, a virtual private network, the Internet, an intranet, an extranet, a public switched telephone network, an infrared network, a wireless network, and any combination thereof.

The computer device 500 can include a variety of data stores and other memory and storage media as discussed above. These can reside in a variety of locations, such as on a storage medium local to (and/or resident in) one or more of the computers or remote from any or all of the computers across the network. In some implementations, information can reside in a storage-area network ("SAN") familiar to those skilled in the art. Similarly, any necessary files for performing the functions attributed to the computers, servers, or other network devices may be stored locally and/or remotely, as appropriate.

In implementations, the components of the computer device 500 as described above need not be enclosed within a single enclosure or even located in close proximity to one another. Those skilled in the art will appreciate that the above-described componentry are examples only, as the computer device 500 can include any type of hardware componentry, including any necessary accompanying firmware or software, for performing the disclosed implementations. The computer device 500 can also be implemented in part or in whole by electronic circuit components or processors, such as application-specific integrated circuits (ASICs) or field-programmable gate arrays (FPGAs).

If implemented in software, the functions can be stored on or transmitted over a computer-readable medium as one or more instructions or code. Computer-readable media includes both tangible, non-transitory computer storage media and communication media including any medium that facilitates transfer of a computer program from one place to another. A storage media can be any available tangible, non-transitory media that can be accessed by a computer. By way of example, and not limitation, such tangible, non-transitory computer-readable media can comprise RAM, ROM, flash memory, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes CD, laser disc, optical disc, DVD, floppy disk and Blu-ray disc where disks usually reproduce data magnetically, while discs reproduce data optically with lasers. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Combinations of the above should also be included within the scope of computer-readable media.

While the teachings have been described with reference to examples of the implementations thereof, those skilled in the art will be able to make various modifications to the described implementations without departing from the true spirit and scope. The terms and descriptions used herein are set forth by way of illustration only and are not meant as limitations. In particular, although the processes have been described by examples, the stages of the processes can be performed in a different order than illustrated or simultaneously. Furthermore, to the extent that the terms "including", "includes", "having", "has", "with", or variants thereof are used in the detailed description, such terms are intended to be inclusive in a manner similar to the term "comprising." As used herein, the terms "one or more of" and "at least one of" with respect to a listing of items such as, for example, A and B, means A alone, B alone, or A and B. Further, unless specified otherwise, the term "set" should be interpreted as "one or more." Also, the term "couple" or "couples" is intended to mean either an indirect or direct connection. Thus, if a first device couples to a second device, that connection can be through a direct connection, or through an indirect connection via other devices, components, and connections.

What is claimed is:

1. A method for phase contrast imaging of an object using an interferometer comprising a multi-sector source grating, a beam-splitter grating, and an analyzer grating, wherein the object is positioned between the beam-splitter grating and the analyzer grating, the method comprising:
   directing an X-ray beam onto the multi-sector source grating, wherein each sector of the multi-sector source grating is offset by a predetermined amount;
   obtaining multiple images during a single exposure by translating the object or the interferometer, wherein the multiple images have a different interferometer phasing; and
   combining the multiple images that were obtained to produce a phase contrast image of the object.

2. The method according to claim 1, wherein the multi-sector source grating has greater than three different sectors.

3. The method according to claim 1, wherein the multiple images are acquired at different angles through the object.

4. The method according to claim 1, wherein the interferometer has a length about 1.8 m.

5. The method according to claim 1, wherein the analyzer grating has a thickness of about several tens of centimeters.

6. The method according to claim 1, wherein the multiple images are obtained using a line detector or a slot scan detector separated by about 1 cm that is positioned behind the analyzer grating.

7. The method according to claim 1, wherein the multiple images of the object are obtained at angular increments of about 0.3°.

8. The method according to claim 1, wherein the multiple images comprises four images and an angular range between the four images is about 0.9°.

9. The method according to claim 1, wherein the analyzer grating comprises multiple glancing angle gratings stacked in order to cover a length of a detector.

10. A device for phase contrast imaging of an object comprising:
    an interferometer comprising a multi-sector source grating, a beam-splitter grating, and an analyzer grating, wherein the object is positioned between the beam-splitter grating and the analyzer grating;
    an X-ray source operable to direct an X-ray bean onto the multi-sector source grating, wherein each sector of the multi-sector source grating is offset by a predetermined amount;
    a translation mechanism operable to translate the object or the interferometer;
    a detector operable to obtain multiple images of the object during a single exposure; and
    a processor operable to combine the multiple images that were obtained to produce a phase contrast image of the object.

11. The device according to claim 10, wherein the multi-sector source grating has greater than three different sectors.

12. The device according to claim 10, wherein the multiple images are acquired at different angles through the object.

13. The device according to claim 10, wherein the interferometer has a length about 1.8 m.

14. The device according to claim 10, wherein the analyzer grating has a thickness of about several tens of centimeters.

15. The device according to claim 10, wherein the detector is a line detector or a slot scan detector and the multiple images are obtained using the line detector or the slot scan detector separated by about 1 cm that is positioned behind the analyzer grating.

16. The device according to claim 10, wherein the multiple images of the object are obtained at angular increments of about 0.3°.

17. The device according to claim 10, wherein the multiple images comprises four images and an angular range between the four images is about 0.9°.

18. The device according to claim 10, wherein the analyzer grating comprises multiple glancing angle gratings stacked in order to cover a length of the detector.

* * * * *